(12) United States Patent
Wu et al.

(10) Patent No.: US 8,030,523 B2
(45) Date of Patent: Oct. 4, 2011

(54) METHOD FOR OBTAINING NATURAL ASTAXANTHIN FROM EGGS AND GONADS OF SNAILS

(75) Inventors: Yi-Lung Wu, Hsinchu (TW); Chin-Chang Yang, Hsinchu (TW)

(73) Assignee: Bioptik Technology, Inc., Hsinchu (TW)

( * ) Notice: Subject to any disclaimer, the term of this patent is extended or adjusted under 35 U.S.C. 154(b) by 558 days.

(21) Appl. No.: 12/205,674

(22) Filed: Sep. 5, 2008

(65) Prior Publication Data

US 2009/0191604 A1 Jul. 30, 2009

(30) Foreign Application Priority Data

Jan. 30, 2008 (TW) .............................. 97103482 A

(51) Int. Cl.
*C07C 45/00* (2006.01)
*C12P 7/26* (2006.01)

(52) U.S. Cl. ...................................... 568/338; 435/148
(58) Field of Classification Search .................. 568/338; 435/148
See application file for complete search history.

(56) References Cited

U.S. PATENT DOCUMENTS

| 3,906,112 | A | 9/1975 | Anderson et al. |
| 4,505,936 | A | 3/1985 | Meyers et al. |
| 4,871,551 | A | 10/1989 | Spencer |
| 5,210,186 | A | 5/1993 | Mikalsen |
| 5,356,810 | A | 10/1994 | Fleno et al. |
| 5,599,711 | A | 2/1997 | Fleno et al. |
| 5,679,567 | A | 10/1997 | Fleno et al. |
| 5,972,642 | A | 10/1999 | Fleno et al. |
| 2007/0196894 | A1 | 8/2007 | Sim et al. |

FOREIGN PATENT DOCUMENTS

| CN | 1824652 | 8/2006 |
| WO | WO 90/05765 | 5/1990 |
| WO | WO2007/029627 A1 | 3/2007 |

OTHER PUBLICATIONS

European search report dated May 14, 2009.
Chokkara Madhu Babu et al., Enzymatic Isolation of carotenoid-protein complex from shrimp head waste and its use as a source of cartenoids, LWT, 2008, pp. 227-235, vol. 41.
Jian-Ping Yuan et al., Hydrolysis Kinetics of Astaxanthin Esters & Stability of Astaxanthin of *Haematococcus pluvialis* during Saponification, J. Agric. Food Chem., 1999, pp. 31-35, vol. 47.
Marcos S. Dreon et al., Astaxanthin binding and structural stability of the apple snail carotenoprotein ovorubin, Archives of Biochemistry and Biophysics, 2007, pp. 107-112, vol. 460.
D.F. Cheesman et al., Carotenoproteins in Invertebrates, Biol. Rev., 1967, pp. 132-160, vol. 42.
Database WPI Week 200708, Thomson Scientific, Zhucheng Lianchun Natural Pigment Extrac, Aug. 30, 2006.
Database WPI Week 200708, Thomson Scientific, Marine Prod Tech Co., Ltd., Nov. 26, 2004.
Synowiecki, J.; Shahidi, F. Isolation of mucopolysaccharides from processing discards of seal and beef... Food Chem. 1994, 51, 89-93.
Lagocka, J.; Sadowska, M.; Synowiecki, J. Separation and characteristics of different mucopolysaccharides from bovine trachea cartilage. Food Chem. 1997, 60, 533-536.
Heras, H.; Pollero, R. J. Lipoproteins from plasma and perivitellin fluid of the apple snail *Pomacea canaliculata*. Bio cell. 2002, 26, 111-118.
Dreon, M. S.; Schinella, G.; Heras, H.; Pollero, R. J. Antioxidant defense system in the apple snail eggs, the role of ovorubin. Arch. Biochem. Biophys. 2004, 422, 1-8.
Chan, J. T.; Patterson, G. W.; Dutky, S. R.; Cohen, C. F. Inhibition of sterol biosynthesis in *Chlorella sorokiniana* by triparanol. Plant Physiol. 1974, 53, 244-249.
Sarada, R.; Vidhyavathi, R.; Usha, D.; Ravishankar, G. A. An efficient for extraction of astaxanthin from green alga *Haematococcus pluvialis*. J. Agric. Food Chem. 2006, 54, 7585-7588.
Kang, C. D.; Sim, S. J. Selective extraction of free astaxanthin from *Haematococcus* culture using a tandem organic solvent system. Biotechnol. Prog. 2007, 23, 866-871.
Khanafari, A.; Saberi, A.; Azar, M.; Vosooghi, Gh.; Jamili, Sh.; Sabbaghzadeh, B. Extraction of astaxanthin esters from shrimp waste by chemical and microbial methods. Iran. J. Environ. Health. Sci. Eng. 2007, 4, 93-98.
Yuan, J. P.; Chen, F. Hydrolysis kinetics of esters and stability of astaxanthin of *Haematococcus pluvialis* during saponification. J. Agric. Food Chem. 1999, 47, 31-35.

*Primary Examiner* — Sikarl Witherspoon
(74) *Attorney, Agent, or Firm* — WPAT, P.C.; Anthony King

(57) ABSTRACT

The present invention relates to a process which can effectively extract and purify natural astaxanthin from the eggs and gonads of snails.

18 Claims, No Drawings

METHOD FOR OBTAINING NATURAL ASTAXANTHIN FROM EGGS AND GONADS OF SNAILS

FIELD OF THE INVENTION

The present invention relates to the extraction and purification of natural astaxanthin from eggs and/or gonads of snails.

BACKGROUND OF THE INVENTION

A lot of research has demonstrated that the capacity of astaxanthin in cleaning free radicals is 10-fold that of β-carotene, and 100-fold that of vitamin E. It was also found that astaxanthin can penetrate the blood brain barrier (BBB) and directly provide an antioxidant effect on the central nervous system of the brain.

At the present time, astaxanthin is mainly chemically synthesized and is used as an animal feed, a nutritional supplement and a food pigment. Since the synthesized astaxanthin contains a specific enantiomer and its effect on human health is not totally understood, there is doubt about whether the synthesized astaxanthin is suitable as an additive in health foods. Therefore, astaxanthin from biological sources will be mainly used in future. Furthermore, in order to encourage the utilization of additives from their natural sources, many European countries and the United States of America are passing legislation to limit the use of chemically synthesized compounds as feed additives.

The known natural sources of astaxanthin are shrimps, crabs, fishes, feathers of birds, yeast, algae, etc. U.S. Pat. No. 3,906,112 discloses a method for extracting astaxanthin from shrimp processing waste which comprises the step of extracting with soybean oil at a temperature of 80-90° C. U.S. Pat. No. 4,505,936 discloses a process for extracting astaxanthin using the steps of removing proteinaceous tissue from the chitinous shell and then extracting astaxanthin from the chitinous shell with a vegetable oil. U.S. Pat. No. 5,210,186 discloses a process for recovering astaxanthin from shrimps and other crayfish by utilizing an alkaline solvent during boiling. CN 1824652 relates to a process for extracting astaxanthin from plants with the utilization of supercritical fluid $CO_2$. U.S. Pat. Nos. 5,599,711, 5,356,810 and 5,972,642 pertain to the processes for extracting astaxanthin from *Phaffia rhodozyma*. Since astaxanthin produced by *P. rhodozyma* is presented in the cell plasma, in order to obtain astaxanthin from cells, they must be treated by a method that can break the cell wall or allow astaxanthin to pass through the cell wall. In such U.S. patents, the yeast cells must be dried and the drying process will increase the complexity of extraction, decrease the production of astaxanthin because of the loss of astaxanthin during the processing, and increase the consumption of energy. U.S. Pat. No. 4,871,551 discloses a method for obtaining astaxanthin from *Heamatococcus pluvialis* with the utilization of suitable organic solvents, e.g., oils, aromatics, halogenated hadrocarbons, and alkanes. WO 2007/029627 discloses a process for extracting astaxanthin from *Heamatococcus pluvialis* with the utilization of supercritical fluid $CO_2$. U.S. Publication No. 2007/0196894 discloses a method for separating free-astaxanthin from *Heamatococcus pluvialis*, and the method comprises the steps of extracting with an alkanic solvent and then extracting with an alcohol.

*Pomacea canaliculata* (Lamarck) (Gastropoda, Ampullariidae), also named apple snail, has become a serious calamity in agriculture around the world because of its strong reproductive capacity and its ability to extend its geographical range. The eggs of the apple snail are spherical and pink to red. It has been found that its eggs and gonads contain a large amount of astaxanthin. The present invention found an effective method to extract and purify the natural astaxanthin from the eggs and gonads of the apple snail.

SUMMARY OF THE INVENTION

The present invention provides a method for obtaining natural astaxanthin from the eggs and gonads of snails.

DETAILED DESCRIPTION OF THE INVENTION

Unless otherwise defined herein, scientific and technical terms used in connection with the present invention shall have the meanings that are commonly understood by those of ordinary skill in the art. The meaning and scope of the terms should be clear. However, in the event of any latent ambiguity, definitions provided herein take precedent over any dictionary or extrinsic definition.

Generally, the methods and techniques of the present invention are performed according to conventional methods well known in the art and as described in various general and more specific references that are cited and discussed throughout the present specification, unless otherwise indicated. Enzymatic reactions are performed according to the manufacturer's specifications, as commonly accomplished in the art or as described herein.

As utilized in accordance with the present disclosure, the following terms, unless otherwise indicated, shall be understood to have the following meanings:

The present invention relates to a process for obtaining astaxanthin from eggs and/or gonads of snails. The process comprises the following steps:

(a) grinding the eggs and/or gonads;

(b) mixing the ground eggs and/or gonads sample with a first solvent and conducting sonication;

(c) removing the solid components in the mixture to obtain a glycol-lipo-carotenoprotein solution;

(d) contacting the glycol-lipo-carotenoprotein solution with a proteinase in the dark under $N_2$ atmosphere so that the proteins are digested;

(e) removing the digested proteins to obtain a glycol-lipo-carotenoid solution;

(f) removing lipids and saccharide compounds from the glycol-lipo-carotenoid solution to obtain a carotenoid solution;

(g) extracting the carotenoid solution with a second solvent to obtain an astaxanthin-containing solution; and (h) purifying astaxanthin from the astaxanthin-containing solution.

According to the present invention, the term "astaxanthin" represents a mixed form of a free form and an ester form having the formula shown below:

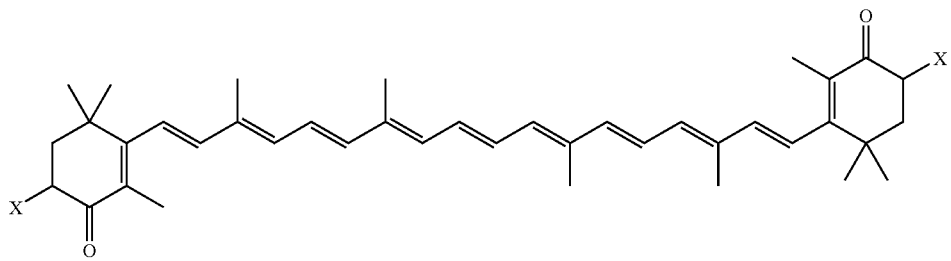

—OH: free-astaxanthin
—OR: astaxanthin ester.

The eggs and gonads of snails used in the present invention are not limited as long as astaxanthin is contained therein. In a preferred embodiment, the eggs and gonads are obtained from the family Ampullariidae, are more preferably obtained from the genera *Pomacea*, and are even more preferably obtained from *Pomacea canaliculata*.

According to the invention, the first solvent can be water or a mixture of water and acetone. In an embodiment of the invention, only snail eggs are used, the first solvent is water, and the ratio (w/v) between the eggs and water is about 1:1 to about 1:5, more preferably about 1:2 to about 1:4, and even more preferably about 1:3. In an another embodiment of the invention, only snail gonads are used, the first solvent is the mixture of water and acetone, the ratio (w/v) between the gonads, acetone and water is about 1:1:3 to about 1:2:3, and preferably about 1:1:3. In a further embodiment of the invention, both eggs and gonads are used, and the first solvent is the mixture of water and acetone. In said first solvent, the volumes of water and acetone depend on the weights of the eggs and the gonads, respectively, as described above.

The proteinase used in Step (d) of the present invention can be any enzymes that can hydrolyze proteins and polypeptides so that they become peptides, oligopeptides and/or amino acids. The conditions of the hydrolysis reaction depend on the species of the proteinase selected. The examples of the proteinase include, but are not limited to, papain, bromelain, thermolysin, pepsin, trypsin bromelain, Alcalase, Flavorzyme, Esperase, and a mixture thereof. The proteinase preferably used is papain or bromelain, and papain is more preferably used. The amount of proteinase added is about 0.5% to about 1.5% (w/v) on the basis of the volume of the glycol-lipo-carotenoprotein solution.

In Step (e) of the invention, the digested proteins can be removed by any methods known in the art. For example, the digested proteins can be precipitated out from the glycol-lipo-carotenoprotein solution by the methods described in Synowiecki et al. (1994) and Lagocka et al. (1997). In an embodiment of the invention, a protein precipitation agent is added to the solution. The protein precipitation agent can be selected from saturated magnesium sulfate, sodium chloride, semi-saturated ammonium sulfate, trichloroacetate, sulfony Salicylate, acetic acid and a concentrated inorganic acid. The amount of the agent added is about 5 to 10% (w/v).

In Step (f) of the invention, lipids and saccharide compounds can be removed by any methods known in the art. For example, lipids and saccharide compounds can be precipitated out from the glycol-lipo-carotenoid solution by the methods described in Lagocka et al. (1997), Heras et al. (2002), Dreon et al. (2004), and Chan et al. (1974). In an embodiment of the invention, a lipid/saccharide precipitation agent is added to the solution. The lipid/saccharide precipitation agent can be selected from acetone, methanol, and ethanol, all of which contain 1% digitonin or 2% Triton X-100. The volume of the precipitation agent added is about 2-fold to about 5-fold that of the glycol-lipo-carotenoid solution.

According to the invention, the precipitates, e.g., the solid components in Step (c), the digested proteins in Step (e) and the lipids and saccharide compounds in Step (f), can be separated from the solutions by any methods known in the art, such as filtration and centrifugation.

The second solvents that can be used in the invention are all organic hydrophobic solvents capable of extracting astaxanthin. For example, solvents can be selected from the group consisting of an edible oil (e.g., soybean oil, peanut oil, olive oil, grape seed oil, corn oil, and sunflower oil), a linear or branched alkane having a carbon number from 6 to 20 (e.g., n-hexane), an alkyl halide (e.g., dichloromethane, trichloromethane and tetrachloromethane), an aromatic (e.g., benzene and toluene), an ester (e.g., ethyl acetate and butyl acetate), and an ether (e.g., ethyl ether).

In Step (h) of the invention, astaxanthin can be purified by any methods known in the art, such as the methods described in Sarada et al. (2006), Kang et al. (2007) and Khanafari et al. (2007). In an embodiment of the invention, astaxanthin is purified by column elution with the utilization of an eluent selected from the group consisting of n-hexane, ethyl acetate, acetone, dichloromethane, methanol, ethanol, ethanenitrile, and a mixture thereof. If an edible oil is used in Step (g) as the second solvent, a linear or branched alkane having a carbon number from 6 to 20 (e.g., n-hexane) or an ether (e.g., ethyl ether) is added to the astaxanthin-containing oil to reduce the viscosity of the oil, and then an absorbent (e.g., silica gel and aluminum oxide) can be used to absorb the astaxanthin contained in the oil.

The present invention further comprises the conversion of the ester form of astaxanthin, including monoester-astaxanthin and diester-astaxanthin, into free-astaxanthin. The conversion can be conducted by any methods known in the art, such as the method described in Yuan et al. (1999), and can be conducted at any time after Step (e). In an embodiment of the invention, an alkaline solution (e.g., 0.1 M NaOH) is added to the reaction of Step (f) to adjust the pH value to about 12 so that the ester form converts to the free form. In an another embodiment of the invention, in order to convert the ester form to the free form an antioxidant (e.g., butyl hydroxyanisole (BHA), butyl hydroxytoluene (BHT), sodium disulfite, vitamin E, and a mixture thereof) is added to the glycol-lipo-carotenoid solution obtained from Step (e) in an amount from about 0.1% to about 1.0% (w/v), and the reaction is conducted in the dark under $N_2$ atmosphere and acidic conditions at about 60° C.

According to the process of the present invention, the first and second solvents used can be recovered so that the operation cost can be reduced.

The following examples are provided to aid those skilled in the art in practicing the present invention. Even so, the examples should not be construed so that they unduly limit the present invention, as modifications and variations in the embodiments discussed herein may be made by those having ordinary skill in the art without departing from the spirit or scope of the present invention.

EXAMPLES

Example 1

The Preparation of Glyco-Lipo-Carotenoprotein Solutions a) The glycol-lipo-carotenoprotein solution prepared from the apple snail eggs:

1,000 g of fresh apple snail eggs were vigorously agitated and milled with 3,000 ml of deionized water under room temperature, and then the obtained homogenous mixture was sonicated for 20 seconds. The sonicated mixture was filtered, and the filtrate was collected to obtain a glycol-lipo-carotenoprotein solution. The glycol-lipo-carotenoprotein solution was stored in a 4° C. dark box under $N_2$ atmosphere in order to avoid contact with air, light and a high temperature.

b) The glycol-lipo-carotenoprotein solution prepared from the apple snail gonads (including albumin glands and ovaries):

1,000 g of fresh apple snail gonads obtained from mature snails were vigorously agitated and milled with 3,000 ml of deionized water and 1,000 ml of acetone under room temperature, and then the obtained homogenous mixture was sonicated for 20 seconds. The sonicated mixture was filtered, and the filtrate and the solid residues were collected separately. The solid residues were further extracted with 250 ml acetone 3 times. The filtrate and the extracts were mixed to obtain a glycol-lipo-carotenoprotein solution. The glycol-lipo-carotenoprotein solution was stored in a 4° C. dark box under $N_2$ atmosphere in order to avoid contact with air, light and a high temperature.

c) The glycol-lipo-carotenoprotein solution prepared from the apple snail eggs and gonads:

600 g of fresh apple snail eggs and 400 g of fresh apple snail gonads were vigorously agitated and milled with 3,000 ml of deionized water and 400 ml of acetone under room temperature, and then the obtained homogenous mixture was sonicated for 20 seconds. The sonicated mixture was filtered, and the filtrate and the solid residues were collected separately. The solid residues were further extracted with 150 ml acetone 3 times. The filtrate and the extracts were mixed to obtain a glycol-lipo-carotenoprotein solution. The glycol-lipo-carotenoprotein solution was stored in a 4° C. dark box under $N_2$ atmosphere in order to avoid contact with air, light and a high temperature.

Example 2

Purifying Astaxanthins from the Glyco-Lipo-Carotenoprotein Solutions

In a dark room under $N_2$ atmosphere, 15 g of papain (Merck Chemicals; Cat. No. 107149.1000, specific activity 30000 USP-U/mg) were added to 1,000 ml each of the glycol-lipo-carotenoprotein solutions obtained from Example 1 and agitated for 24 hours. Each digested solution was filtrated, the filtrate was collected and the solid residues were removed. 120 ml 10% acetic acid were dropped into each filtrate. Each mixture was agitated in a dark room under $N_2$ atmosphere for 3 hours, and then the mixture was filtrated to remove the precipitate containing the digested proteins. An ethanol solution containing 2% TritonX-100 with a volume three times greater than each of the filtrates was added to each filtrate, and then the mixture was filtrated to remove the precipitate containing lipids and saccharide compounds. The filtrates were concentrated and the ethanol contained therein was recovered by decompression. Astaxanthin contained in each concentrated filtrate was extracted by n-hexane. The organic phases were washed by 100 ml deionized water several times, and then dried by anhydrous sodium sulfate. Astaxanthin mixtures were obtained through a decompressing concentrating process. The components of the astraxanthin mixtures were analyzed by Thin Layer Chromatography (TLC; 0.25 mm precoated sheet) with a mobile phase of n-hexane:acetone (4:1). Free-astaxanthin, monoester-astraxanthin and diester-astraxanthin were observed from the TLC graph. Further studies found that the free-astaxanthin obtained from the column chromatography analysis (silica gel (70-230 mesh), eluent (n-hexane:ethyl acetate:acetone=10:2:1)) has the following characteristics:

3,3'-Dihydroxy-β,β-carotene-4,4'-dione, dark purple needle crystal, mp: 181~183° C., UV-vis λmax 485 nm ($CHCl_3$), and $^1H$ NMR($CHCl_3$) 400 MHz δ(ppm) 1.21 (s, 6H, $C(CH_3)_2$), 1.32 (s, 6H, $C(CH_3)_2$), 1.81 (t, J=13.6 Hz, 2H, $CH_2CHOH$), 1.94 (s, 6H, =C($H_3$)CO), 1.99 (s, 6H, $CH_3C$=CH), 2.00 (s, 6H, $CH_3C$=CH), 2.16 (dd, J=5.6, 12.5 Hz, 2H, $CH_2CHOH$), 3.49 (s, 2H, OH), 4.32 (dd, J=5.6, 13.6 Hz, 2H, CHOH), 6.19-6.46 (m, 10H, =CH), 6.62-6.69 (m, 4H, =CH).

Example 3

Selective Extraction and Purification of Free-Astaxanthin—Ester Astaxanthins were Hydrolyzed Under Alkaline Conditions In a dark room under $N_2$ atmosphere, 15 g of papain (Merck Chemicals; Cat. No. 107149.1000, specific activity 3000USP-U/mg) were added to 1,000 ml of the glycol-lipo-carotenoprotein solution obtained from (a) of Example 1 and agitated for 24 hours. The digested solution was filtrated to remove the solid residues. 120 ml of 10% acetic acid were dropped into the filtrate. The mixture was agitated in a dark room under $N_2$ atmosphere for 3 hours, and then the mixture was filtrated to remove the precipitate containing the digested proteins. An ethanol solution containing 2% TritonX-100 with a volume three-fold that of the filtrate was added to the filtrate, and the pH thereof was adjusted to 12 by the addition of 0.1 M NaOH. The solution was than incubated in ice for 8 hours to allow lipids and saccharide compounds contained therein to precipitate and simultaneously allow the ester astaxanthins to be hydrolyzed. TLC analysis was used to determine the completion of the hydrolysis reaction. After the reaction was completed, the product was filtrated to remove the precipitate and obtain an astaxanthin-containing hydrophilic solution. The solution was concentrated and the ethanol contained therein was recovered by decompression. Astaxanthin contained in the concentrated solution was extracted by n-hexane. The organic phase was washed by 100 ml deionized water several times, and then dried by anhydrous sodium sulfate. 40 mg of astaxanthin were obtained through a decompressing concentrating process. The astaxanthin compound was analyzed by TLC (0.25 mm precoated sheet) with a mobile phase of n-hexane:acetone (4:1). It was found that monoester-astraxanthin and diester-astraxanthin were both transformed into free-astaxanthin. Further studies found that the free-astaxanthin obtained has spectral information identical to that of the standard.

Example 4

Selective Extraction and Purification of Free-Astaxanthin—Ester Astaxanthins were Hydrolyzed Under Acidic conditions In a dark room under $N_2$ atmosphere, 15 g of papain (Merck Chemicals; Cat. No. 107149.1000, specific activity 30000USP-U/mg) were added to 1,000 ml of the glycol-lipo-carotenoprotein solution obtained from (a) of Example 1 and agitated for 24 hours. The digested solution was filtrated to remove the solid residues. 120 ml of 10% acetic acid were dropped into the filtrate. The mixture was agitated in a dark room under $N_2$ atmosphere for 3 hours, and then the mixture was filtrated to remove the precipitate containing the digested proteins. Antioxidants, 2 g of butyl hydroxyanisole (BHA) and 3 g of butyl hydroxytoluene (BHT), were added to the filtrate, and the reactant was kept in a 60° C. dark room under $N_2$ atmosphere and agitated for 12 hours to allow the ester astaxanthins to be hydrolyzed. TLC analysis was used to determine the completion of the hydrolysis reaction. After the reaction was completed, the product was cooled to room temperature. An ethanol solution containing 2% TritonX-100 with a volume three-fold that of the product was added to the product, and then the mixture was filtrated to remove the precipitate containing lipids and saccharide compounds and an astaxanthin-containing hydrophilic solution was obtained. The solution was concentrated and the ethanol contained therein was recovered by decompression. Astaxanthin contained in the concentrated solution was extracted by n-hexane. The organic phase was washed by 100 ml deionized water several times, and then dried by anhydrous sodium sulfate. 35 mg of astaxanthin were obtained through a decompressing concentrating process. Further studies found that the free-astaxanthin obtained has spectral information identical to that of the standard.

Example 5

Extraction of Astaxanthins from the Apple Snail Eggs and Gonads by Edible Oil 1,000 ml of soybean oil were added to 1,000 ml of a astaxanthin-containing hydrophilic solution obtained from apple snail eggs and gonads, with proteins, lipids and saccharide compounds already removed from the solution, and then the mixture was mixed by vigorous agitation in a dark room under $N_2$ atmosphere. When the red color of the aqueous phase disappeared after a 36-hour extraction, the aqueous phase and the oil phase were separated from each other by a separatory funnel, so that an astaxanthin-containing soybean oil sample was obtained. The astaxanthin-containing soybean oil was then diluted 10-fold with soybean oil. According to the UV-Vis absorption spectrum (400-700 nm), the astaxanthin-containing soybean oil showed an absorption peak at 480 nm.

According to the process described above, astaxanthin-containing hydrophilic solutions were extracted by olive oil, grape seed oil, corn oil, and sunflower oil, respectively. The rates of astaxanthin extracted by the above oils were determined and calculated on the basis of data obtained from the UV-Vis absorption spectrum. The extraction rates are shown in Table 1 below.

TABLE 1

| Edible Oils | Astaxanthin Extraction Rates (%) |
|---|---|
| olive oil | 92.2 |
| soybean oil | 90.3 |
| corn oil | 88.7 |
| grape seed oil | 85.9 |
| sunflower seed oil | 84.5 |

Example 6

Purification of Astaxanthins Extracted by Edible Oil 100 ml of n-hexane were added to 500 ml of the astaxanthin-containing soybean oil obtained from Example 5 so that the viscosity of the soybean oil was reduced. 20 g of silica gel (70-230 mesh) were added to the sample during agitation until the color of astaxanthin in the sample transferred to the silica gel. The silica gel was washed with 50 ml n-hexane and the step was repeated 3 times to wash off the soybean oil. The silica gel was then treated with decompression so that the solvent attached thereon was removed. The astaxanthin absorbed in the silica gel was eluted by 50 ml 95% ethanol, and the elution step was repeated 3 times. After the ethanol samples were collected, ethanol was removed to obtain a solid of astaxanthin.

Alternatively, the silica gel absorbed with astaxanthin was placed into an empty column, and the column was then washed by an eluent (n-hexane:acetone=4:1) so as to obtain the purified free-astaxanthin. It was found that the purified free-astaxanthin has spectral information identical to that of the standard.

REFERENCE

1. Synowiecki, J.; Shahidi, F. Isolation of mucopolysaccharides from processing discards of seal and beef. *Food Chem.* 1994, 51, 89-93.
2. Lagocka, J.; Sadowska, M.; Synowiecki, J. Separation and characteristics of different mucopolysaccharides from bovine trachea cartilage. *Food Chem.* 1997, 60, 533-536.
3. Heras, H.; Pollero, R. J. Lipoproteins from plasma and perivitellin fluid of the apple snail *pomacea canaliculata*. *Bio cell.* 2002, 26, 111-118.
4. Dreon, M. S.; Schinella, G.; Heras, H.; Pollero, R. J. Antioxidant defense system in the apple snail eggs, the role of ovorubin. *Arch. Biochem. Biophys.* 2004, 422, 1-8.
5. Chan, J. T.; Patterson, G. W.; Dutky, S. R.; Cohen, C. F. Inhibition of sterol biosynthesis in *Chlorella sorokiniana* by triparanol. *Plant Physiol.* 1974, 53, 244-249.
6. Sarada, R.; Vidhyavathi, R.; Usha, D.; Ravishankar, G. A. An efficient for extraction of astaxanthin from green alga *Haematococcus pluvialis*. *J. Agric. Food Chem.* 2006, 54, 7585-7588.
7. Kang, C. D.; Sim, S. J. Selective extraction of free astaxanthin from *Haematococcus* culture using a tandem organic solvent system. *Biotechnol. Prog.* 2007, 23, 866-871.
8. Khanafari, A.; Saberi, A.; Azar, M.; Vosooghi, Gh.; Jamili, Sh.; Sabbaghzadeh, B. Extraction of astaxanthin esters from shrimp waste by chemical and microbial methods. *Iran. J. Environ. Health. Sci. Eng.* 2007, 4, 93-98.
9. Yuan, J. P.; Chen, F. Hydrolysis kinetics of esters and stability of astaxanthin of *Haematococcus pluvialis* during saponification. *J. Agric. Food Chem.* 1999, 47, 31-35.

What is claimed is:

1. A process for obtaining astaxanthin from eggs and/or gonads of snails comprising the steps of:
    (a) grinding the eggs and/or gonads;
    (b) mixing the ground eggs and/or gonads sample with a first solvent while conducting sonication;
    (c) removing the solid components in the mixture to obtain a glycol-lipo-carotenoprotein solution;
    (d) contacting the glycol-lipo-carotenoprotein solution with a proteinase in the dark under $N_2$ atmosphere so that the proteins are digested;
    (e) removing the digested proteins to obtain a glycol-lipo-carotenoid solution;
    (f) removing lipids and saccharide compounds from the glycol-lipo-carotenoid solution to obtain a carotenoid solution;
    (g) extracting the carotenoid solution with a second solvent to obtain an astaxanthin-containing solution; and
    (h) purifying astaxanthin from the astaxanthin-containing solution.

2. The process of claim 1, wherein the snail is *Pomacea canaliculata*.

3. The process of claim 1, wherein astaxanthin is obtained from the snail eggs, and the first solvent is water.

4. The process of claim 1, wherein astaxanthin is obtained from the snail gonads, and the first solvent is a mixture of water and acetone.

5. The process of claim 1, wherein astaxanthin is obtained from the snail eggs and gonads, and the first solvent is a mixture of water and acetone.

6. The process of claim 1, wherein the proteinase is selected from the group consisting of papain, bromelain, thermolysin, pepsin, trypsin bromelain, subtilisin carlsberg, carboxypeptidase OcpB, subtilisin lentus, and a mixture thereof.

7. The process of claim 1, wherein a precipitation agent selected from the group consisting of saturated magnesium sulfate, sodium chloride, semi-saturated ammonium sulfate, trichloroacetate, sulfony Salicylate, acetic acid and a concentrated inorganic acid is added in Step (e) so that the digested proteins precipitate out from the glycol-lipo-carotenoprotein solution.

8. The process of claim 1, wherein a lipid/saccharide precipitation agent selected from the group consisting of acetone, methanol and ethanol, all of which contain 1% digitonin or 2% Triton X-100, is added in Step (f) so that lipids and saccharide compounds precipitate out from the glycol-lipo-carotenoid solution.

9. The process of claim 1, wherein the second solvent is an edible oil, a linear or branched alkane having a carbon number from 6 to 20, an alkyl halide, an aromatic, an ester, or an ether.

10. The process of claim 9, wherein the second solvent is an edible oil selected from the group consisting of soybean oil, peanut oil, olive oil, grape seed oil, corn oil, and sunflower oil.

11. The process of claim 9, wherein the second solvent is a linear or branched alkane having a carbon number from 6 to 20.

12. The process of claim 11, wherein the second solvent is n-hexane.

13. The process of claim 1, wherein step (h) comprises the processes of adding a linear or branched alkane having a carbon number from 6 to 20 or an ether into the astaxanthin-containing solution when the second solvent used in step (g) is an edible oil; and adding an absorbent to absorb the astaxanthin contained in the oil.

14. The process of claim 13, wherein the absorbent is selected from the group consisting of silica gel and aluminum oxide.

15. The process of claim 1, which further comprises a process for converting astaxanthin to free-astaxanthin.

16. The process of claim 15, wherein the conversion process comprises adding an alkaline solution to the glycol-lipo-carotenoid solution so that the pH of said solution becomes about 12.

17. The process of claim 15, wherein the conversion process comprises adding an antioxidant to the glycol-lipo-carotenoid solution, and setting said solution in the dark under $N_2$ atmosphere and acidic conditions at about 60° C.

18. The process of claim 17, wherein the antioxidant is selected from the group consisting of butyl hydroxyanisole (BHA), butyl hydroxytoluene (BHT), sodium disulfite, vitamin E, and a mixture thereof.

* * * * *